(12) United States Patent
Ito et al.

(10) Patent No.: US 9,870,611 B2
(45) Date of Patent: Jan. 16, 2018

(54) DRUG INSPECTION DEVICE

(71) Applicant: YUYAMA MFG. CO., LTD., Toyonaka-shi, Osaka (JP)

(72) Inventors: Koji Ito, Toyonaka (JP); Hiromichi Tsuda, Toyonaka (JP); Hirokazu Amano, Toyonaka (JP); Yasuyuki Yoshikawa, Toyonaka (JP); Mei Zhang, Toyonaka (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 348 days.

(21) Appl. No.: 14/646,879

(22) PCT Filed: Nov. 21, 2013

(86) PCT No.: PCT/JP2013/081353
§ 371 (c)(1),
(2) Date: Sep. 21, 2015

(87) PCT Pub. No.: WO2014/080966
PCT Pub. Date: May 30, 2014

(65) Prior Publication Data
US 2016/0005160 A1   Jan. 7, 2016

(30) Foreign Application Priority Data
Nov. 22, 2012   (JP) .................................. 2012-256015

(51) Int. Cl.
*H04N 7/18*   (2006.01)
*G06T 7/00*   (2017.01)
(Continued)

(52) U.S. Cl.
CPC ....... *G06T 7/0004* (2013.01); *G01N 21/9508* (2013.01); *G06F 19/3456* (2013.01);
(Continued)

(58) Field of Classification Search
CPC .............. G06T 7/0004; G01B 21/9508; G06F 19/3456; G06K 9/00
(Continued)

(56) References Cited

U.S. PATENT DOCUMENTS 4,791,655 A * 12/1988 Nagata ................. G01N 23/043
378/51
6,324,253 B1 * 11/2001 Yuyama ................ G01N 23/04
209/589
(Continued)

FOREIGN PATENT DOCUMENTS

EP   2 702 978 A1   3/2014
JP   07-200770 A    8/1995
(Continued)

*Primary Examiner* — Mishawn Hunter
(74) *Attorney, Agent, or Firm* — Masuvalley & Partners

(57) ABSTRACT

Embodiments of the present invention provide a high accuracy medicament inspection device and system to inspect medicaments enclosed in a package with a printing area. The medicament inspection device implements a medicament information detection process that includes: a medicament candidate area extraction step extracting a dark colored area in a back side illuminated image as a medicament candidate area A (assumed presence of medicament); a print candidate area extraction step extracting an area containing the print on the package based on a front side illuminated image as a print candidate area B; a print area identification step specifying an area corresponding to the print contained in the print candidate area B based on the brightness distribution of the back side illuminated image as a print area C; and a medicament area identification step identifying a medicament area X by subtracting the print area C from the medicament candidate area A.

9 Claims, 16 Drawing Sheets

(51) Int. Cl.

| | | |
|---|---|---|
| *G01N 21/95* | (2006.01) | |
| *G06Q 10/06* | (2012.01) | |
| *G06Q 10/08* | (2012.01) | |
| *G06Q 50/22* | (2012.01) | |
| *G06K 9/00* | (2006.01) | |
| *G06Q 50/24* | (2012.01) | |
| *G06K 9/46* | (2006.01) | |
| *G06K 9/62* | (2006.01) | |
| *H04N 5/225* | (2006.01) | |
| *G06F 19/00* | (2011.01) | |

(52) U.S. Cl.
CPC ............... *G06K 9/00* (2013.01); *G06K 9/46* (2013.01); *G06K 9/4604* (2013.01); *G06K 9/4652* (2013.01); *G06K 9/4661* (2013.01); *G06K 9/6201* (2013.01); *G06Q 10/06* (2013.01); *G06Q 10/087* (2013.01); *G06Q 50/22* (2013.01); *G06Q 50/24* (2013.01); *G06T 7/001* (2013.01); *H04N 5/2256* (2013.01); *H04N 7/18* (2013.01); *G06K 2009/4666* (2013.01)

(58) Field of Classification Search
USPC .......................................................... 348/86
See application file for complete search history.

(56) References Cited

U.S. PATENT DOCUMENTS

| | | | | |
|---|---|---|---|---|
| 6,330,351 B1* | 12/2001 | Yasunaga | ........... | G01N 21/9508 235/375 |
| 8,215,557 B1 | 7/2012 | Reno et al. | | |
| 2006/0213816 A1* | 9/2006 | Jorritsma | ........... | G01N 21/9508 209/576 |
| 2006/0271237 A1* | 11/2006 | Kim | ........ | B65B 5/103 700/226 |
| 2007/0000805 A1* | 1/2007 | Van Den Brink | ....... | G06K 9/00 206/531 |
| 2007/0150093 A1* | 6/2007 | Nagatsuka | ............. | B25J 9/1682 700/235 |
| 2009/0055116 A1* | 2/2009 | Chen | .................. | G01N 21/9508 702/82 |
| 2010/0045976 A1* | 2/2010 | Jorritsma | ........... | G01N 21/9508 356/240.1 |
| 2010/0170206 A1* | 7/2010 | Kim | ........ | B65B 61/28 53/525 |
| 2010/0175352 A1* | 7/2010 | Soloman | ................ | B65B 5/103 53/508 |
| 2010/0175968 A1* | 7/2010 | Yagyu | .................... | B65G 27/02 198/761 |
| 2010/0214560 A1* | 8/2010 | Yagyu | ................ | B65G 47/1421 356/237.1 |
| 2012/0200596 A1 | 8/2012 | Gotou et al. | | |
| 2012/0293623 A1* | 11/2012 | Nygaard | ............... | G06T 7/0004 348/46 |
| 2012/0296592 A1* | 11/2012 | Luciano, Jr. | ........... | B65D 75/36 702/84 |
| 2013/0057677 A1* | 3/2013 | Weil | ....................... | G01N 21/90 348/125 |
| 2013/0342676 A1* | 12/2013 | Amano | .................... | H04N 7/18 348/86 |

FOREIGN PATENT DOCUMENTS

| | | |
|---|---|---|
| JP | 07-209196 A | 8/1995 |
| WO | 2012/147907 A1 | 11/2012 |

* cited by examiner

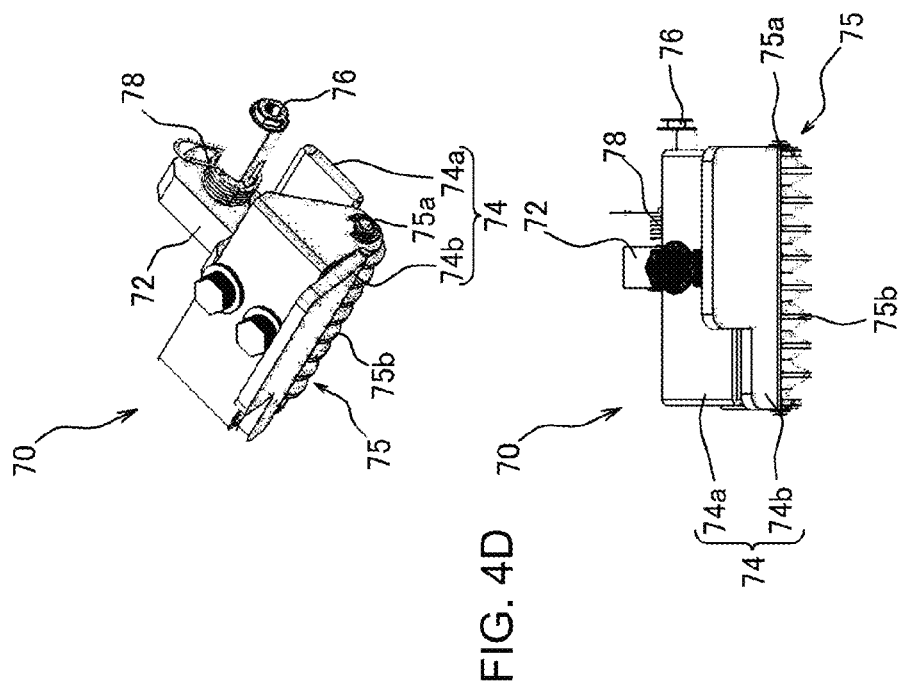
FIG. 4B
FIG. 4D
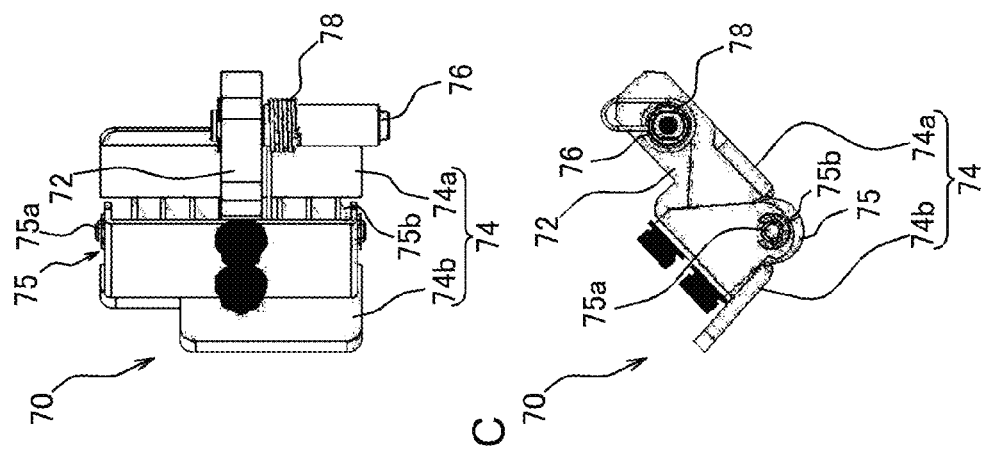
FIG. 4A
FIG. 4C

DRUG INSPECTION DEVICE

This application is a national phase application under 35 U.S.C. §371 of International Application Serial No. PCT/JP2013/081353 filed on Nov. 21, 2013. This application claims priority under 35 U.S.C. §119 to Japan Patent Application JP 2012-256015 filed on Nov. 22, 2012. All these applications are herein incorporated by reference.

TECHNICAL FIELD

The present invention relates to a medicament inspection device for inspecting the number of medicaments, and a medicament packing device equipped with the medicament inspection device.

BACKGROUND OF THE INVENTION

Patent Document 1 (Japanese Patent Application Publication H07-200770) discloses a tablet inspection system. This tablet inspection system can pack one dose of solid medicaments, in a granular form and a capsular form, in a pouch of a packaging sheet. Furthermore, this tablet inspection system is configured to take pictures of the packed solid medicaments, and to inspect the number of the solid medicaments based on the pictures taken.

SUMMARY OF THE INVENTION

As described above, the tablet inspection system of the Patent Document 1 takes the pictures of the solid medicaments, which are individually packed in the pouch of the packaging sheet. When there is a print on the packaging sheet, it is difficult to distinguish an area corresponding to the print and an area corresponding to the medicament in the picture. This difficulty lowers the inspection accuracy. Traditional medicament inspection devices including the tablet inspection system of Patent Document 1 lack a measure to distinguish the area corresponding to the print and the area corresponding to the medicament. Because of this, the traditional medicament inspection devices cannot obtain sufficient inspection accuracy.

Therefore, the purpose of the present invention is to provide a medicament inspection device that can inspect medicaments enclosed in a package, which has a print, with a sufficient accuracy, as well as a medicament packing system equipped with the medicament inspection device.

The medicament inspection device according to the embodiments of the present invention includes: an inspection section where a medicament enclosed in a unit-dose package is placed; a camera device for taking an image of the package paced in the inspection section; an illuminating device for illuminating the package placed in the inspection section; and a control device for executing a medicament information detection process by performing an image matching process to the image obtained by the camera device and by detecting a number and/or a type of the medicament as a medicament information. The illuminating device includes: a front side illuminating device for illuminating the package placed in the inspection section from the camera device side; and a back side illuminating device for illuminating the package from a back surface side of the package. The control device extracts an image of the medicament in the package based on a front side illuminated image taken by the camera device with the front side illuminating device being ON, and based on a back side illuminated image taken by the camera device with the back side illuminating device being ON, and the control device detects the medicament information based on these images. The medicament information detection process includes: a medicament candidate area extraction step for extracting a dark colored area of the back side illuminated image as a medicament candidate area A where the medicament is assumed to be present; a print candidate area extraction step for extracting an area containing a print provided on the package based on the front side illuminated image as a print candidate area B; a print area identification step for identifying an area corresponding to the print contained in the print candidate area B as a print area C based on a brightness distribution of the back side illuminated image; and a medicament area identification step for identifying a medicament area X by subtracting the print area C from the medicament candidate area A.

The medicament inspection device of the present invention obtains the medicament area X by subtracting the print area C specified in the print area identification step from the medicament candidate area A specified in the medicament candidate area extraction step. Moreover, to obtain the print area C, the medicament inspection device first implements the print candidate area extraction step, and narrows down to the area containing the print provided on the package based on the front side illuminated image as a print candidate area B. Then, the medicament inspection device implements the print area identification step, and identifies the area corresponding to the print contained in the print candidate area B as the print area C based on the brightness distribution of the back side illuminated image. In short, the medicament inspection device according to the embodiments of the present invention narrows down to the print area C from the perspectives of both the front side illuminated image and the back side illuminated image. Thus, the accuracy of identifying the print area C is high. Therefore, the medicament inspection device of the present invention can accurately identify the medicament area X, and thus inspect the medicament with high accuracy.

In the above-described medicament inspection device, the medicament candidate area A, where the medicament is assumed to be present, is preferably obtained by the medicament candidate area extraction step by implementing the process of converting the back side illuminated image to a grey scale and acquiring a grey back side illuminated image; binarizing the grey back side illuminated image as an assumed print and medicament area where the presence of the medicament and the print on the package is assumed; obtaining a sum region, which is a sum of a top hat region obtained by top-hat processing the grey back side illuminated image and a bottom hat region obtained by bottom-hat processing the grey back side illuminated image, as an assumed print area where the presence of the print is assumed; and obtaining the medicament candidate area A, which is by a difference between the assumed print and medicament area and the assumed print area.

By dynamically binarizing the grey back side illuminated image obtained from the back side illuminated image as described above, the assumed print and medicament area where the print and the medicament are assumed to be present becomes a black colored area, and can be distinguished from a background region, which is converted to a white color. Moreover, an area where the print is assumed to be present (assumed print area) can be obtained by acquiring a sum region of the top hat region and the bottom hat region obtained by top-hat processing and bottom-hat processing the grey back side illuminated image. Accordingly, by subtracting the assumed print area from the assumed print and medicament area specified by the processes described above, the medicament candidate area A where the medicament is assumed to be present can be specified.

Moreover, in the print candidate area extraction step, the above-described medicament inspection device preferably performs bottom-hat processing for each of an R-channel image, a G-channel image, and a B-channel image obtained through RGB decomposition of the front side illuminated image, and extracts an area assumed to be black in every image including the R-channel image, the G-channel image, and the B-channel image as the print candidate area B.

The medicament inspection device, according to the embodiments of the present invention, utilizes the fact that the black colored print is recognized to be a black color in every image including the R-channel image, the G-channel image, and the B-channel image obtained by subjecting the front side illuminated image to the RGB decomposition. And, the medicament inspection device implements the print candidate area extraction step by focusing on the ability to differentiate between the print candidate area B and other area because of this recognition. Therefore, according to the medicament inspection device of the present invention, the print candidate area B can be extracted.

Upon extracting the print candidate area B as described above, if a possibility is considered that a stamp or the like placed on the medicament to show a lot number or the like can be erroneously recognized as a print provided on the package, an inspection can be performed with even higher accuracy. Based on this assumption, after various measures to differentiate between the stamp or the like on the medicament and the print on the package were examined, it was found that the stamp or the like on the medicament can be excluded from the print candidate area B by utilizing the difference of brightness in the front side illuminated image.

The medicament inspection device of the present invention provided based on the above findings performs the print area identification step including a step of narrowing down to the print area C from an assumed print area derived as a sum region that is a sum of a top hat region obtained by top-hat processing the grey back side illuminated image, which is obtained by converting the back side illuminated image to a grey scale image, and a bottom hat region obtained by bottom-hat processing the grey back side illuminated image. The print area identification step also includes a brightness threshold defining step which analyzes the brightness distribution of the assumed print area in the front side illuminated image, and defines the brightness threshold to distinguish an area corresponding to text and other area. The print area identification step further includes a narrow-down step that obtains the print candidate area B assumed to be a black color in every image including the R-channel image, the G-channel image, and the B-channel image obtained through RGB decomposition of the front side illuminated image, and narrows down to the print area C included in the print candidate area B in the front side illuminated image based on the brightness threshold obtained by the brightness threshold defining step.

In the medicament inspection device of the present invention, the print area identification step is executed through a brightness threshold defining step and a narrow-down step. The brightness threshold defining step includes a step of obtaining the brightness threshold to differentiate between the area corresponding to text and other area by applying the assumed print area derived by the same method explained for executing the above-described medicament candidate area extraction step to the front side illuminated image. The narrow-down step include the step of applying the print candidate area B obtained by the same method as that in the print candidate area extraction step to the front side illuminated image, and narrowing down to the print area C contained in the print candidate area B in the front side illuminated image based on the brightness threshold obtained by the brightness threshold defining step. By implementing these processes, it is possible to accurately distinguish the stamp or the like placed on the medicament and the print provided on the package. Thus, the stamp or the like on the medicament is prevented from being included in the print area C.

Here, according to the embodiments of the present invention, the medicament to be inspected is photographed in the state of being contained in the package. Therefore, due to the influence of an image of a wrinkle of the package or a striation which appears unexpectedly by the reflection of light can lead to the recognition of a plurality of medicaments even if only a single medicament is present. Hence, in order to further improve the inspection accuracy of the medicament inspection device, some sort of measure to eliminate such a possibility is preferable.

The medicament inspection device of the present invention provided based on this finding has an inspection area defining step which stipulates an area to be inspected based on the medicament area X obtained in the medicament area identification step. The inspection area defining step is preferably implemented through steps of obtaining a reduced medicament candidate area A2 which is an area where the medicament candidate area A has been reduced, and obtaining a sum region of the medicament area X and the reduced medicament candidate area A2 as a medicament inspection area Z.

In the inspection area defining step, the medicament inspection device of the present invention obtains the reduced medicament candidate area A2 obtained by reducing the medicament candidate area A, and obtains the sum region of the medicament area X and the reduced medicament candidate area A2 as the medicament inspection area Z. Thereby, it is possible to prevent the medicament area X for a single medicament from being divided and detected into multiple areas erroneously. Thus, the inspection accuracy of the medicament is improved.

Moreover, the medicament inspection device according to the embodiments of the present invention can execute an image matching process using an image database in which images capturing the medicaments are accumulated as master images. The medicament inspection device has a master image creation process capable of creating a master image of a divided medicament based on a master image showing an entire shape of the medicament. The master image creation process includes: a contour acquisition step of obtaining a contour of the entire shape of the medicament based on the back side illuminated image of the medicament to be registered; an entire image acquisition step of acquiring an image in an area corresponding to an internal area of the contour in the front side illuminated image obtained by the contour acquisition step as an image of the entire shape of the medicament; a background brightness derivation step of recognizing an image in the front side illuminated image that corresponds to an external area of the contour obtained by the contour acquisition step as a background image, and obtaining an average brightness of the background image; and overlay step of creating a masking image having a brightness corresponding to the background image obtained by the background brightness derivation step, and overlaying the masking image in a portion of the area of the image of the entire shape of the medicament obtained by the entire image acquisition step.

By the master image creation process, the medicament inspection device of the present invention can acquire the master image of the medicament divided into a plurality based on the master image showing the entire shape of the single medicament. The medicament inspection device, according to the embodiments of the present invention, first performs the contour acquisition step to obtain the contour pertaining to the entire shape derived from the back side illuminated image. Then, the medicament inspection device performs the process (entire image acquisition step) to apply this contour to the front side illuminated image and thereby acquire the entire image of the medicament. Next, the medicament inspection device performs the process (background brightness derivation step) of recognizing the image of the exterior area of the contour in the front side illuminated image as a background image, and obtaining the average brightness of the background image. Lastly, the medicament inspection device performs the overlay step of making a masking image based on the obtained average brightness, and overlaying the masking image in a portion of the area of the image pertaining to the entire shape of the medicament obtained by the entire image acquisition step. Thereby, the master image of the divided medicament is obtained. According to the embodiments of the present invention, the master image showing the divided medicament is accurately created from the master image showing the entire shape.

To specify the type of the medicament by the comparison using an image database in which images of the medicaments are accumulated as master images, there is a possibility that the specification of the medicament may not be successful because the color tones may differ between the registered master image and the actual image photographed by the camera device. In other words, even if the same medicament is photographed, color tones may be different due to individual differences of camera devices and illuminating devices. Resulting from this, an inspection problem may arise.

The medicament inspection device of the present invention is provided with the assumption of such a circumstance. Thus, the medicament inspection device can compare the photographed medicament with an image database in which photographed images of the medicaments are accumulated as master images. More specifically, the medicament inspection device can compare the image of the medicament placed in the inspection section and photographed by the camera device with a master image of this medicament. In the case where the control device decides that the captured image of the medicament and the master image of this medicament is not the same, the control device creates a new master image of this medicament based on the image photographed by the camera device and replaces the already registered master image with this newly created master image.

By the above-described configuration, it is possible to prevent inspection errors originating from differences of color tones between the master image registered in the image database and the image actually photographed.

The medicament packing system, according to the embodiments of the present invention, is provided with the above-described medicament inspection device and a medicament packaging device for packing the medicaments in an individual unit dose of pouch in a package in accordance with a prescription. The medicament inspection device can inspect the quantity of medicaments, which are individually packed in the package by the medicament packaging device.

The medicament packing system of the present invention can accurately carry out a series of tasks from packing the medicaments individually to inspecting the packed medicaments.

According to the embodiments of the present invention, it is possible to provide a medicament inspection device, which can inspect the medicaments enclosed in the package that has a print with a sufficient accuracy, as well as a medicament packing system equipped with the medicament inspection device.

BRIEF DESCRIPTION OF THE DRAWINGS

FIGS. 4A-4D are diagrams showing a modified embodiment of a medicament laying device. FIG. 4A is a plan view, FIG. 4B is a perspective view, FIG. 4C is a front view, and FIG. 4D is a side view.

FIG. 14A shows an image that shows a contour depicting the entire shape of the medicament, and FIG. 14B shows an image that shows a shape of the medicament divided approximately equally into two.

DETAILED DESCRIPTION OF THE INVENTION

Figure 1A:
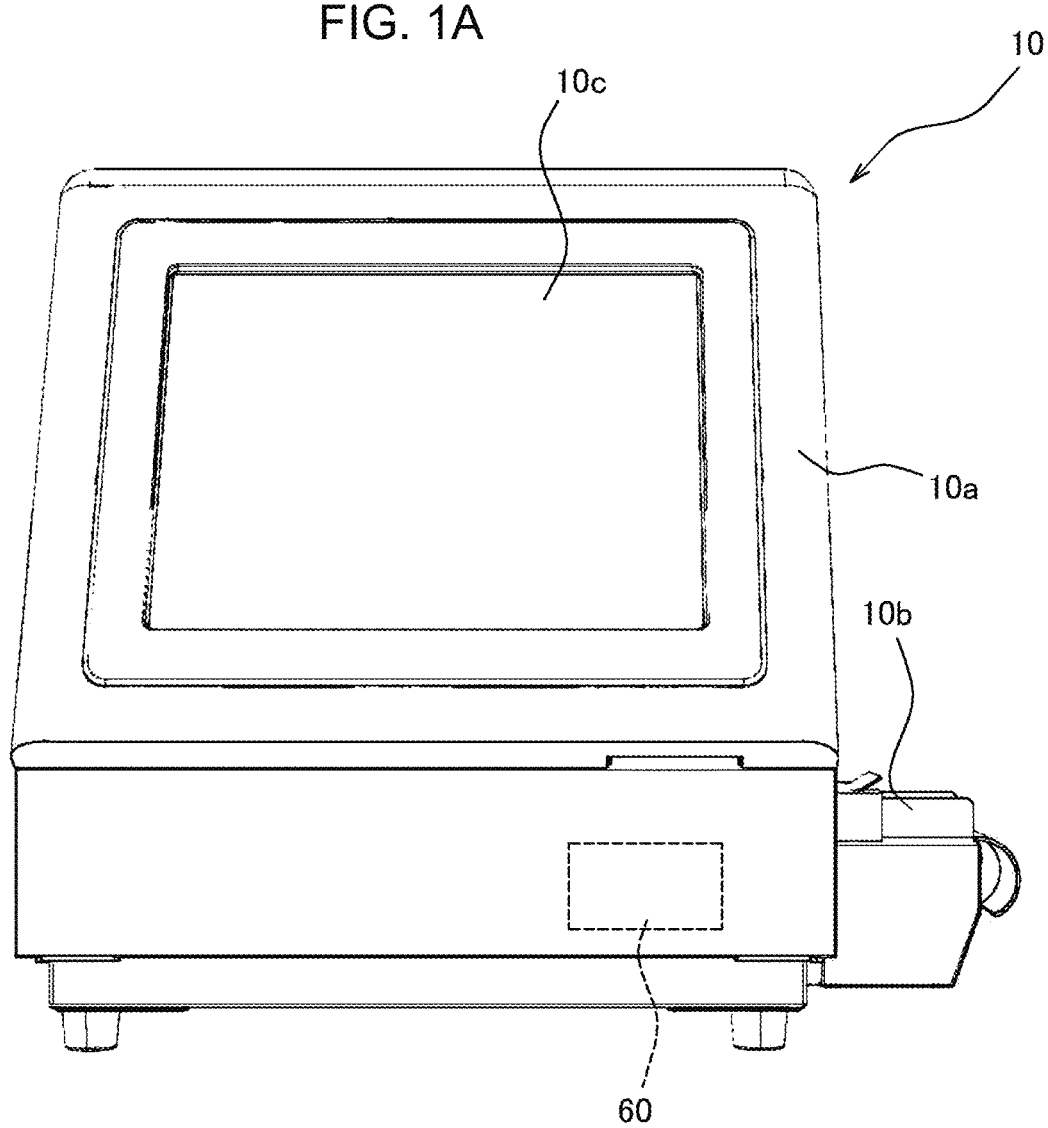
FIG. 1A is a front view of an embodiment of a medicament inspection device.

Referring to the drawings, a medicament inspection device 10, according to one embodiment of the present invention, is described in detail below. The medicament inspection device 10 is a device that inspects the number and type of medicaments in a single dose unit package. The medicaments are packed in pouches of a packaging sheet on dose-by-dose basis. And, these medicaments enclosed in the pouches are supplied to the medicament inspection device 10. As shown in FIG. 1A, the medicament inspection device 10 has a housing 10a, and an introduction unit 10b provided on the lateral side of the housing 10a. The medicaments are introduced in the medicament inspection device 10 through this introduction unit 10b. Furthermore, an operation panel 10c is provided on the front side of the housing 10a. The medicaments are packaged in a translucent packaging sheet and supplied to the medicament inspection device 10 at the state visible from outside. Moreover, the medicament inspection device 10 can supply a pouch chain B, which is comprised of a chain of pouches b connected to each other. Each pouch b contains a dose of medicaments. Then, the medicament inspection device 10 can inspect the pouches b one by one.

Figure 1B:
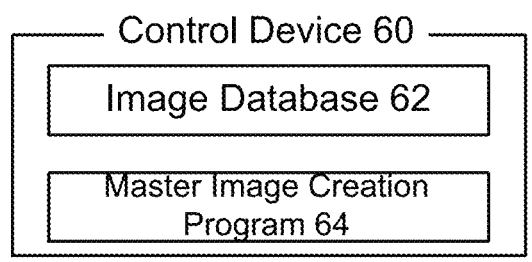
FIG. 1B is a block diagram of a control device the medicament inspection device has.
Figure 2:
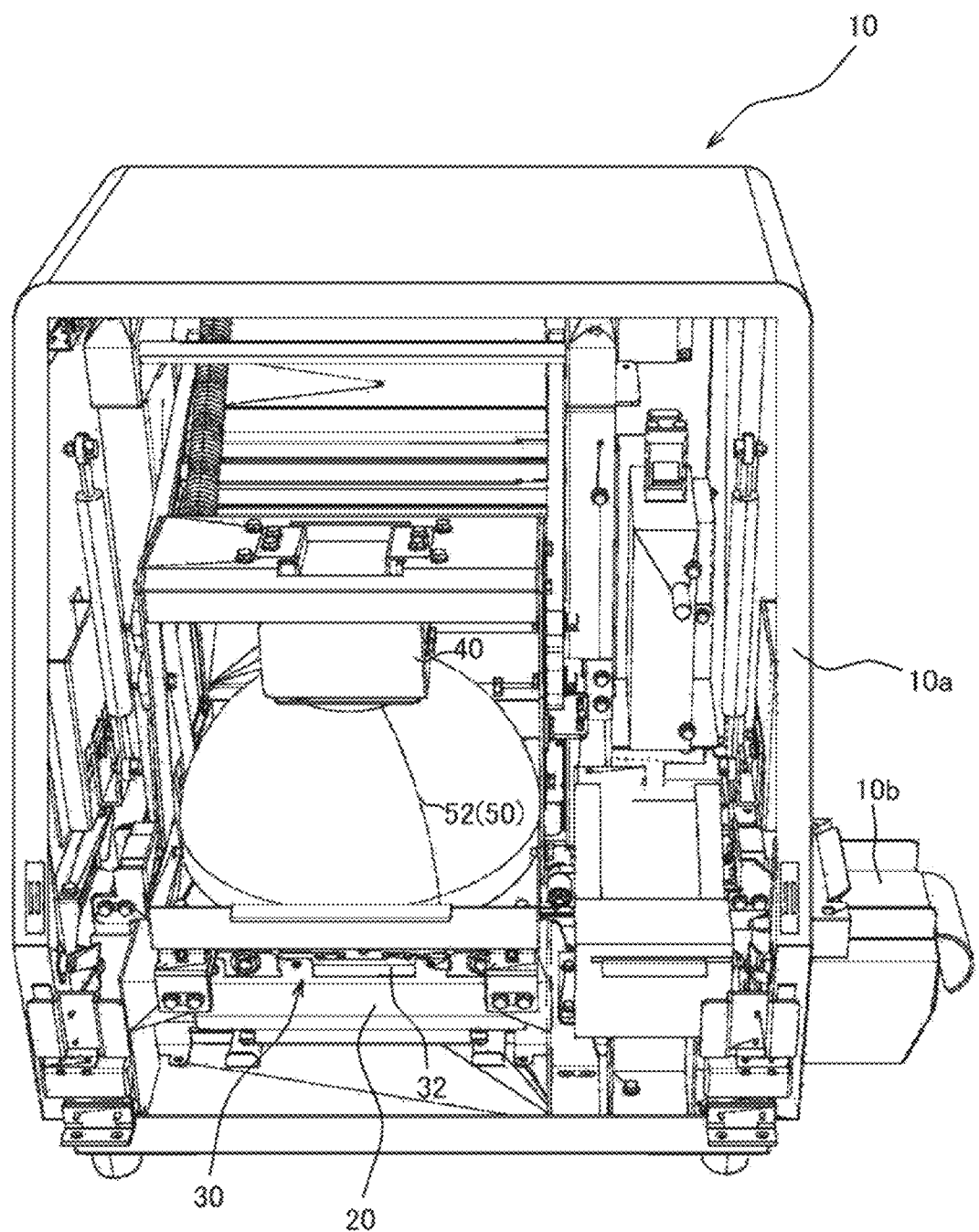
FIG. 2 is a perspective view showing an internal structure of the medicament inspection device.
Figure 3:
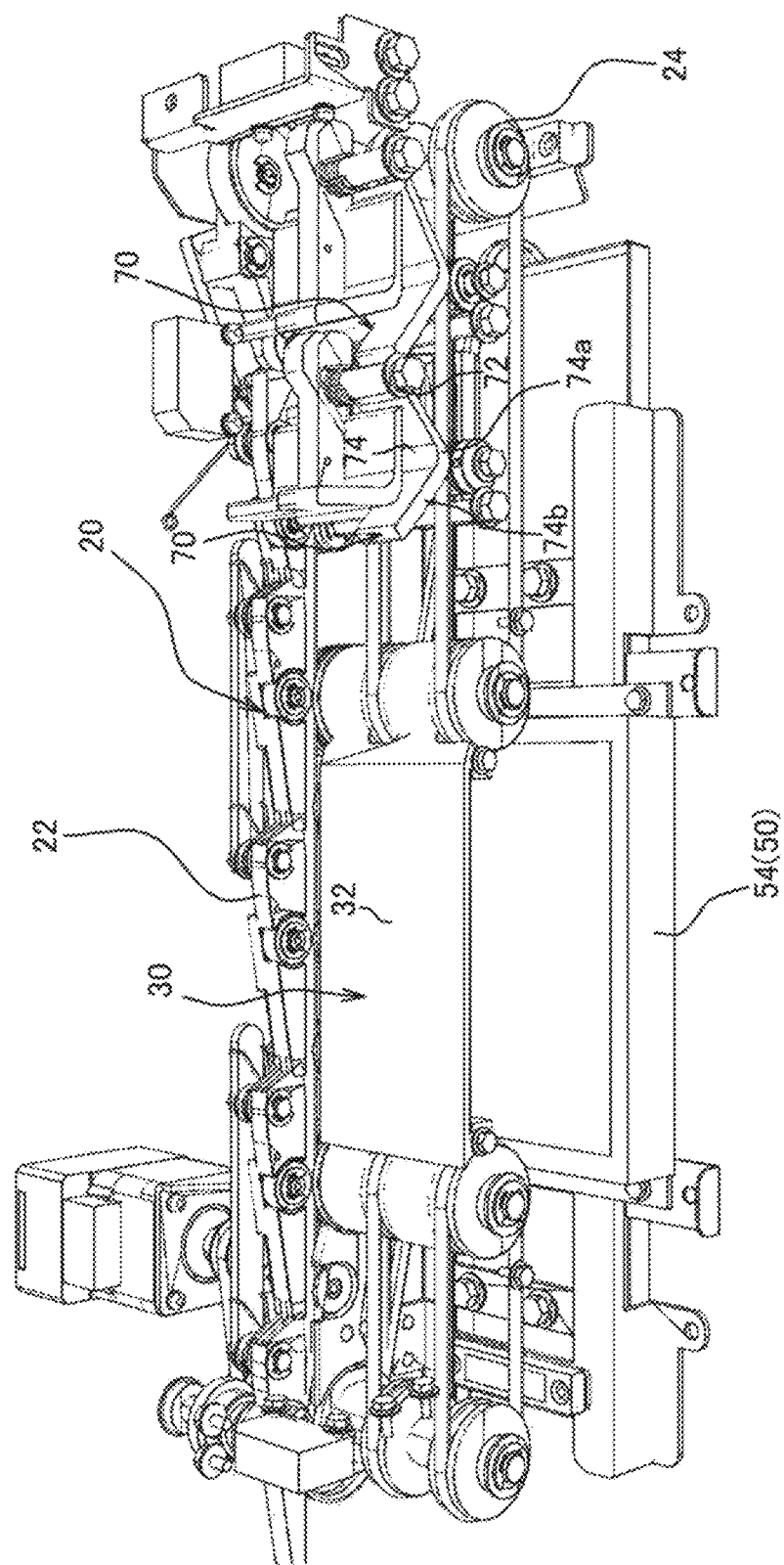
FIG. 3 is a perspective view showing a structure in the vicinity of an inspection section of the medicament inspection device.

As shown in FIG. 1 to FIG. 3, the medicament inspection device 10 has a conveyer device 20, an inspection section 30, a camera device 40, an illuminating device 50, and a control device 60. The conveyer device 20 receives and transports the pouch chain B. The conveyer device 20 can be set up with a conventional belt conveyor, roller conveyor, or the like. In the present embodiment, a belt conveyor is employed for the conveyer device 20. When the pouch chain B is detected by a supply detection device (not shown in the drawings), which is provided in the upstream of the inspection section 30 with respect to the conveyance direction, the conveyer device 20 conveys the pouch chain B in the downstream direction under the control of the control device 60, which will be described further below. Furthermore, the conveyer device 20 stops its operation when a discharge detection device (not shown in the drawings), which is provided in the downstream of the inspection section 30, confirms that the end of the pouch chain B comprised of the packaging sheet is discharged in the downstream of the inspection section 30.

The inspection section 30 is a place where the medicaments to be inspected are placed at the state of being enclosed in the pouch b. As shown in FIG. 3, the inspection section 30 has a photographing stage 32, on which the pouch b is placed. The photographing stage 32 is made of a transparent plate and has a size capable of loading the pouch b, which corresponds to one dose. The camera device 40 takes a picture of the pouch b placed in the inspection section 30 including the medicaments enclosed in the pouch b. As shown in FIG. 2, the camera device 40 is provided directly above the inspection section 30.

The illuminating device 50 illuminates the pouch b placed in the inspection section 30. The illuminating device 50 has a front side illuminating device 52 (shown in FIG. 2) and a back side illuminating device 54 (shown in FIG. 3). The front side illuminating device 52 illuminates the pouch b in the inspection section 30 from the side where the camera device 40 is located, in other words, from the top of the inspection section 30. The front side illuminating device 52 may be configured with any type of illuminating device. In the present embodiment, an illuminating device capable of generating diffused light is used for the front side illuminating device 52. The back side illuminating device 54 illuminates the pouch b in the inspection section 30 from the back side, in other words from the side opposite to the camera device 40 across (below) the inspection section 30. The back side illuminating device 54 illuminates almost entire region of the photographing stage 32 as well as the entire pouch b placed on the photographing stage 32 from the back side.

The control device 60 is realized by means of a computer in which software is installed. The control device 60 can execute processes such as medicament inspection process to inspect whether the medicaments enclosed in each pouch b are correct in accordance with the prescription.

In addition to the above-mentioned basic components, the medicament inspection device 10 of the present embodiment also has additional components such as a medicament laying device 70 (shown in FIG. 3 and FIGS. 4A-4D). The medicament laying device 70 lays down a standing or erected medicament inside the pouch b. The medicament laying device 70 is located in the upstream of the inspection section 30 and can lay down the standing medicament by following the front surface of the packaging sheet, which is conveyed by the conveyer device 20. The medicament laying device 70 may be any configuration. In the present embodiment, its configuration is shown in FIGS. 4A-4D.

More specifically, the medicament laying device 70 has an arm 72. At an end of the arm 72 is provided a contact portion 74, whose side view is approximately a V-shape. The arm 72 is rotatably mounted on a support shaft 76, which orients in a transverse direction of the conveyer path. The arm 72 is also biased towards the conveyer path by a spring 78. Thereby, the contact portion 74 of the arm 72 can touch the front surface of the packaging sheet moving along the conveyer path with a moderate force of strength so that it does not damage the packaging sheet and the medicaments.

The contact portion 74 has an introduction side inclined surface 74a, a discharge side inclined surface 74b and a medicament laying tool 75. The introduction side inclined surface 74a is facing the upstream side of the conveyance direction, and the discharge side inclined surface 74b faces the downstream side of the conveyance direction. The introduction side inclined surface 74a forms an acute angle θ1 to the upper surface of the conveyer path formed by the conveyer device 20 as well as the pouch chain B (pouch b) transported on the conveyer path. The discharge side inclined surface 74b forms an acute angle θ2 to the upper surface of the conveyer path and the pouch chain B.

The medicament laying tool 75 is provided between the introduction side inclined surface 74a and the discharge side inclined surface 74b. The medicament laying tool 75 has a support shaft 75a and balls 75b. The support shaft 75a extends along a boundary portion formed between the edges of the introduction side inclined surface 74a and the discharge side inclined surface 74b. In other words, the support shaft 75a is approximately orthogonal to the conveying direction of the pouch chain B. The balls 75b have a sphere-like shape such as bead or abacus sphere. In the present embodiment, the balls 75b have an appearance similar to an abacus bead, whose cross-sectional shape is hexagonal or approximately rhombic and whose external appearance is as if bottom surfaces of two truncated cones are joined to each other. The balls 75b are mounted on the support shaft 75a so that they can slide along the support shaft 75a.

Because of this configuration, reciprocation of the pouch chain B causes the ball 75b contacting the medicament to slide along the support shaft 75a. Because of this axial movement, the ball 75*b* gently touches the medicament. Thereby, the ball 75*b* lays down the standing medicament, making it easier to inspect.

Figure 5:
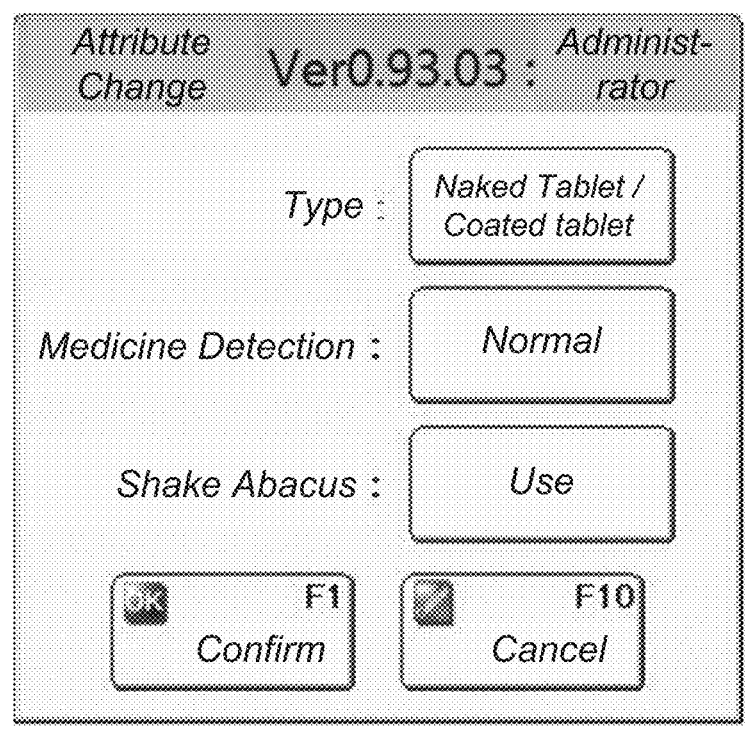
FIG. 5 is an image showing an example of an interface displayed by the medicament inspection device.

The medicament inspection device 10 may be configured to always use the medicament laying tool 75 but also to provide choices to use or not to use the medicament laying tool 75. The way to provide the choices may be any. One example is shown in FIG. 5, in which an operation screen of the medicament inspection device 10 displays an interface that provides the user the choices to use or not to use the medicament laying tool 75. In the case of FIG. 5, the user can select to use or not to use the medicament laying tool 75 by touching the button corresponding to the item displayed as "Shake Abacus".

When there is no need to lay down the medicaments but the medicament laying tool 75 is contacting the packaging sheet conveyed by the conveyer device 20, a random load is constantly incurred to the packaging sheet (pouch chain B) from the medicament laying tool 75. This might cause the pouch chain B to come off the conveyer path during the middle of the inspection.

When the medicament inspection device 10 is configured to provide the choices to use or not to use the medicament laying tool 75, as the example of FIG. 5, it is desirable to configure the medicament inspection device 10 so that the medicament laying tool 75 can retract from the conveyer path formed by the conveyer device 20. In this case, when the above-described situation is concerned to happen and there is no need to use the medicament laying tool 75, the medicament laying tool 75 is operated to stay away from the packaging sheet.

Figure 15:
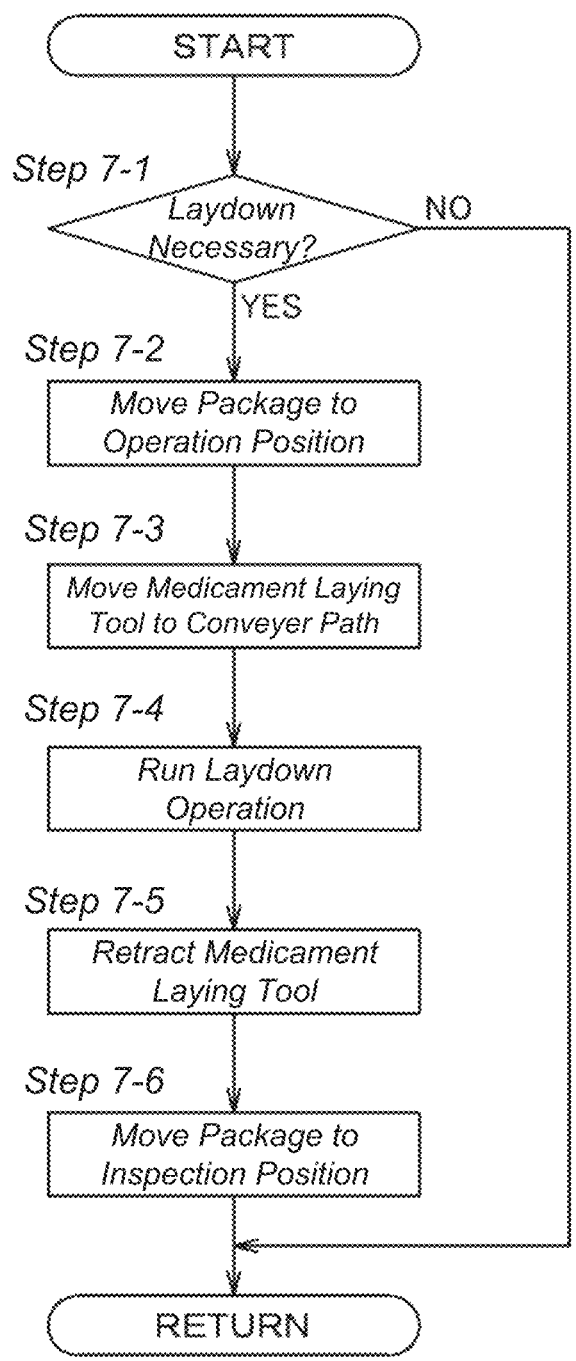
FIG. 15 is a flowchart showing an example of an operation, which enables a medicament laying tool to be retracted from a conveyer path.

More specifically, at the initial stage, the medicament laying tool 75 is at the state of being retracted from the conveyer path. Then, as shown in FIG. 15, in Step 7-1, first it is determined whether a "laydown operation", which lays down the medicaments, is necessary. The determination method can be based on the above-described setting status or the usage condition of the medicament laying tool 75. Furthermore, the determination method can also be based on the way of image processing described later.

In Step 7-1, once it is detected that the medicaments contained in the package need to be laid down, the package subjected to the laydown operation is moved to a laydown operation position (in Step 7-2), which is a place where the contact portion 74 is provided. Then, in Step 7-3, the medicament laying tool 75 is moved to inside of the conveyer path of the conveyer device 20. In this state, in Step 7-4, the pouch chain B is reciprocated in upstream and downstream directions of the conveyer path. Thereby, the medicaments in the package are laid down. Next, in Step 7-5, the medicament laying tool 75 is retracted from the conveyer path. Lastly, in Step 7-6, the package is moved to the inspection place. Then, the inspection operation is conducted as usual.

As described above, if the medicament laying tool 75 is able to retract from the conveyer path based on necessity, the force incurred to the pouch chain B can be minimized. Therefore, it is possible to prevent the come-off of the pouch chain B from the conveyer path. This prevents the occurrence of an inspection error. In addition, the medicaments standing inside the package can be appropriately laid down by the laydown operation.

While the pouch chain B is reciprocated by the medicament laying tool 75 to lay down the standing medicament, a wrinkle can be formed on the pouch chain B. In addition, in the present embodiment, as shown in FIG. 3, clamps 22 are provided in the conveyer device 20 along one transverse end of the surface (conveyer path) of the conveyer to hold the pouch chain B. However, there are no items corresponding to the clamps 22 in the other end portion. Therefore, when the pouch chain B comes off the clamps 22 by the reciprocating motion, the wrinkle can be easily formed on the pouch chain B. Once the wrinkle is formed on the pouch chain B, not only does its appearance become bad, but a concern also arises that the accuracy of the inspection implemented at the inspection section 30 may decrease. Under worst case conditions, the pouch chain B may come off the conveyer path, and as a result, it may become jammed in the device.

Figure 16A:
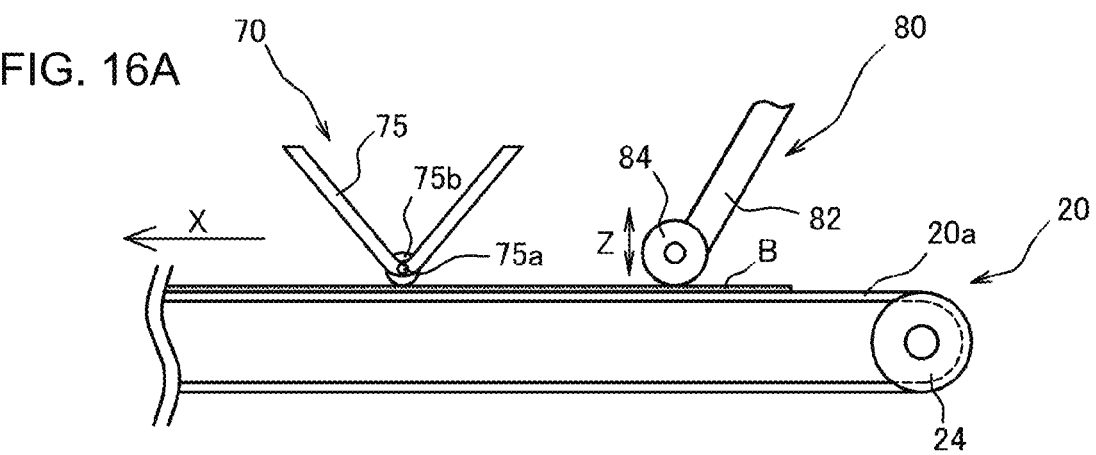
FIG. 16A is a side view showing a state where a packaging sheet pressing tool is provided, with key parts enlarged.
Figure 16B:
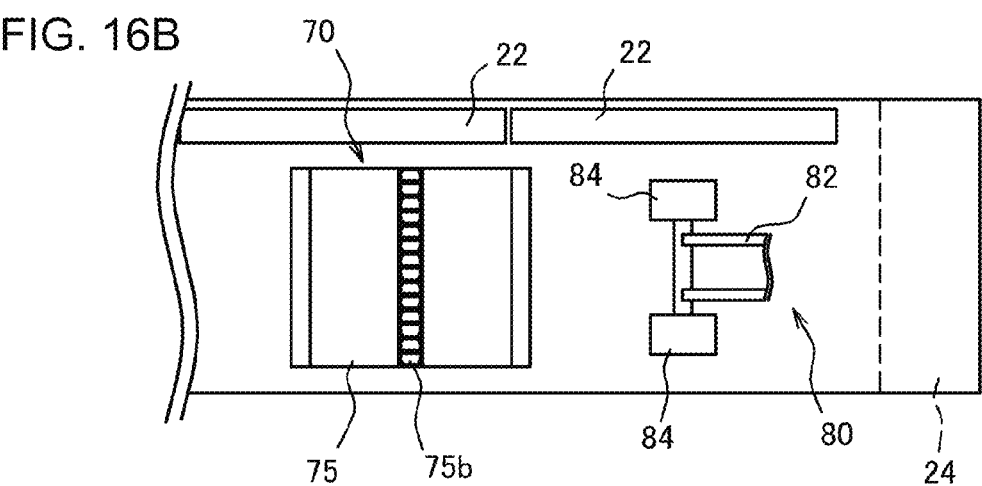
FIG. 16B is a plan view of FIG. 16A.

Therefore, when there is a concern that the wrinkle is formed on the pouch chain B, it is desirable to provide a configuration as those shown in FIGS. 16A and 16B. More specifically, a packaging sheet pressing tool 80 is provided on the conveyer path and at a place distant from the medicament laying tool 75. The packaging sheet pressing tool 80 contacts the pouch chain B and applies a force that presses the pouch chain B toward a conveyer surface 20*a* of the conveyer device 20, allowing the reciprocating motion of the pouch chain B in the conveyance direction (direction of arrow X in FIG. 16A). In the present embodiment, the packaging sheet pressing tool 80 is provided in the upstream side of the medicament laying tool 75 with respect to the conveyance direction. Furthermore, the packaging sheet pressing tool 80 is provided between the medicament laying tool 75 and a driving roller 24 of the conveyer device 20. The packaging sheet pressing tool 80 is biased toward the conveyer surface 20*a* by a spring or other biasing item (not shown in the drawing). The biasing force acting on the packaging sheet pressing tool 80 is of a degree such that the packaging sheet pressing tool 80 can move up and down (see arrow Z in FIG. 16A), following the surface of the pouch chain B that is passing under the packaging sheet pressing tool 80.

In the present embodiment, as shown in FIG. 3 and FIG. 16B, the clamps 22 are provided in one transverse end portion of the conveyer device 20. Therefore, by providing the packaging sheet pressing tool 80 at a place distant from the clamps 22 in respect to the transverse direction of the conveyer device 20, plural places of the pouch chain B are held along the transverse direction, and thus the pouch chain B is prevented from coming off the conveyer path of the conveyer device 20. And thereby, the formation of the wrinkle on the pouch chain B is prevented.

Furthermore, as shown in FIGS. 16A and 16B, by providing rollers 84 on a main body 82 of the packaging sheet pressing tool 80 so that the rollers 84 contact to the pouch chain B, the reciprocating motion of the pouch chain B can be smoother. In addition, the wrinkle formed on the pouch chain B can be smoothed out by the roller 84.

Figure 16C:
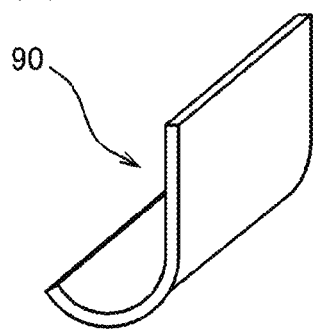
FIG. 16C and FIG. 16D are perspective views showing modified examples of the packaging sheet pressing tool.
Figure 16D:
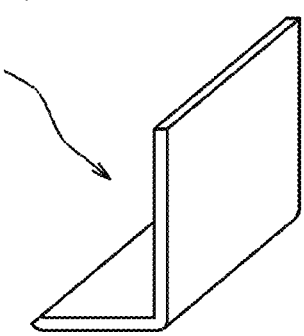

Although FIGS. 16A and 16B show an example of the packaging sheet pressing tool 80 in which the rollers 84 are attached to the main body 82, the present invention is not limited to this configuration. As long as the packaging sheet pressing tool is the one that can contact the pouch chain B and apply a pressing force toward the conveyer surface of the conveyer device 20 as well as allow the reciprocating motion of the pouch chain B in the conveyance direction, any type of the packaging sheet pressing tool may be used such as the packaging sheet pressing tools 90 and 100 shown in FIGS. 16C and 16D, in which plate bodies are formed in a J-shape and an L-shape respectively. Moreover, the rollers 84 do not necessarily have to be provided at the contact portions of the pouch chain B. In this case, however, it is desirable to use a metal, resin, or the like that can smoothly slide on the pouch chain B.

In the example shown in FIG. 16B, two rollers 84 are provided along the transverse direction of the conveyer device 20. However, the number of rollers 84 can be modified. Furthermore, the packaging sheet pressing tool 80 has a configuration in which the rollers 84 contact the portions (two places in the present embodiment) of the pouch chain B that are aligned in the transverse direction of the pouch chain B. However, the packaging sheet pressing tool 80 may have a configuration that can contact a portion of the pouch chain B that extends across the entire width of the pouch chain B.

<Medicament Inspection Process>

As shown in FIG. 1B, the control device 60 is equipped with an image database 62, which stores accumulated images of medicaments as master images. The control device 60 can execute a medicament information detection process to detect the number (quantity) and/or a type of a medicament as medicament information by executing an image matching process, which matches an image of the medicament captured by the camera device 40 with a master image registered in the image database 62. Below, an overview of the medicament information detection process is described first. Then, substeps in each step are described in more detail.

<Medicament Information Detection Process>

Figure 6A:
FIGS. 6A-6H are images showing examples of the images obtained in the steps of a medicament information detection process.
Figure 6B:
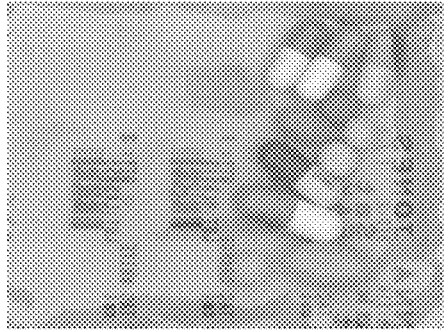

A medicament information detection process is implemented using a front side illuminated image captured by the camera device 40 with the front side illuminating device 52 being ON as well as a back side illuminated image captured by the camera device 40 with the back side illuminating device 54 being ON. As shown in FIG. 6B, the front side illuminated image is a front view image of the pouch b, and it shows an image capturing an appearance of the medicament and a print provided on the pouch b. As shown in FIG. 6A, the back side illuminated image shows an image that captures the silhouette of the medicament and the print on the pouch b. The control device 60 extracts an image of the medicament contained in the pouch b based on the front side illuminated image and the back side illuminated image. Then, the control device 60 detects the medicament information based on the image of the medicament.

Figure 6C:
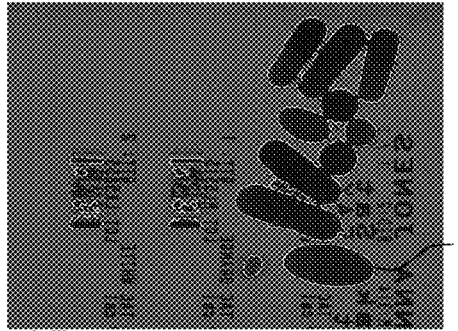
Figure 6D:
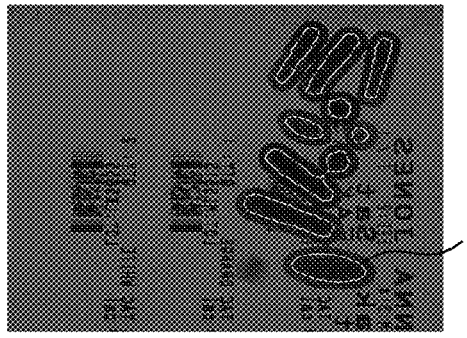
Figure 6E:
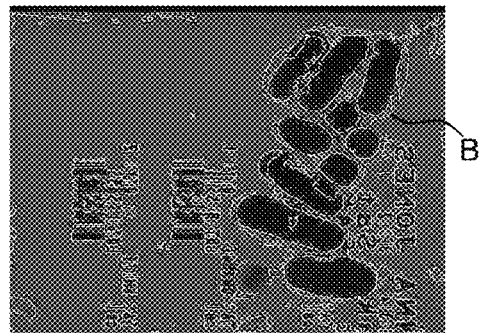
Figure 7:
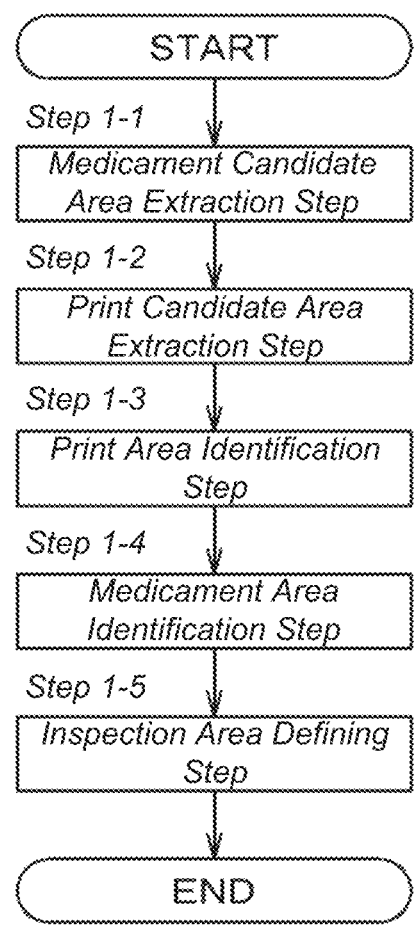
FIG. 7 is a flowchart showing a main routine of the medicament information detection process.

As shown in FIG. 7, the medicament information detection process is overall carried out through a medicament candidate area extraction step (Step 1-1), a print candidate area extraction step (Step 1-2), a print area identification step (Step 1-3), a medicament area identification step (Step 1-4), and an inspection area defining step (Step 1-5). The medicament candidate area extraction step implemented in Step 1-1 is a step to extract an area that contains the medicament as a medicament candidate area A from the back side illuminated image (see FIG. 6C). The print candidate area extraction step implemented in Step 1-2 is a step to extract an area that contains the print provided on the package as a print candidate area B (see FIG. 6E) from the front side illuminated image.

Figure 6F:
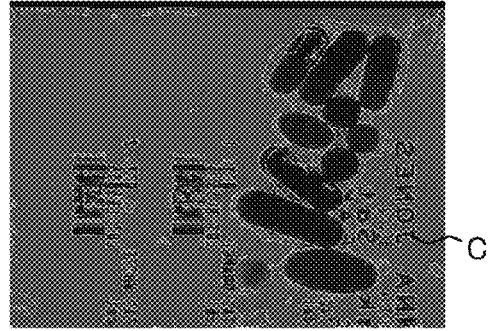
Figure 6G:
Figure 6H:

The print area identification step implemented in Step 1-3 is a step to identify an area corresponding to the print contained in the print candidate area B as a print area C (see FIG. 6F) based on the brightness distribution of the back side illuminated image. The medicament area identification step implemented in Step 1-4 is a step to identify a medicament area X (see FIG. 6H) by subtracting the print area C obtained in Step 1-3 from the medicament candidate area A obtained in Step 1-1. Lastly, the inspection area defining step implemented in Step 1-5 is a step to define an area that is to be inspected based on the medicament area X obtained by the medicament area identification step.

Figure 8:
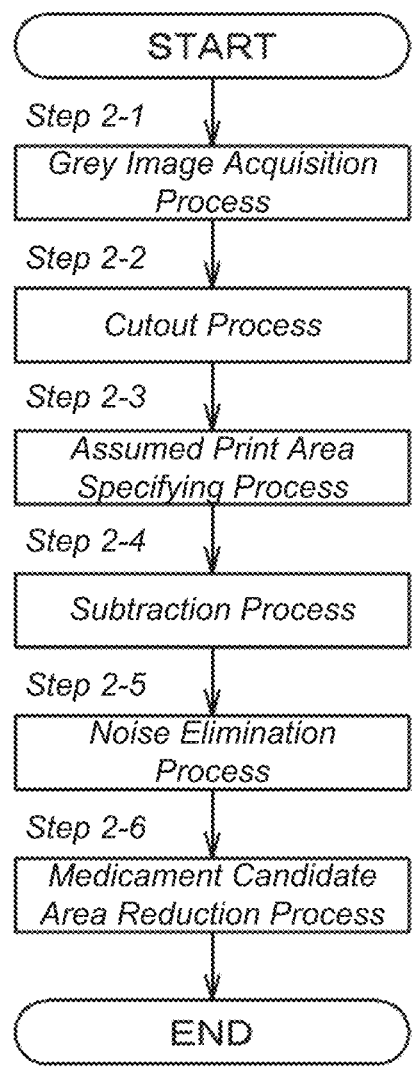
FIG. 8 is a flowchart showing the medicament candidate area extraction step, which is a subroutine of the medicament information detection process.

Below, each step (image processing) shown in FIG. 7 is described in more detail. As shown in FIG. 8, Step 1-1 of the medicament information detection process is implemented through a grey image acquisition process (Step 2-1), a cutout process (Step 2-2), an assumed print area specifying process (Step 2-3), a subtraction process (Step 2-4), a noise elimination process (Step 2-5), and a medicament candidate area reduction process (Step 2-6).

More specifically, when the control flow of the main routine (shown in FIG. 7) is at Step 1-1, a subroutine, the grey image acquisition process of Step 2-1 (shown in FIG. 8) is executed first. The grey image acquisition process is a process that acquires a grey back side illuminated image by converting the back side illuminated image into a grey scale image. Next, the control flow proceeds to Step 2-2, and the cutout process is executed. This is a process to cut out an assumed print and medicament area, in which the medicament and the print on the pouch b are assumed to be present, by dynamically binarizing the grey back side illuminated image obtained in Step 2-1. The silhouette of the medicament and the print are constituted with black or dark colors in the grey back side illuminated image, and the background is constituted with a white or light colors. Therefore, by subjecting the grey back side illuminated image to the dynamic binarization, the area where the print and medicament are present (black colored region) can be separated from the background area (white colored region).

Once the cutout process in Step 2-2 is complete, the control flow proceeds to Step 2-3, and the assumed print area specifying process is implemented. In the assumed print area specifying process, a region brighter than its surroundings (top hat region) is obtained by subjecting the grey back side illuminated image to a top-hat process. In addition, a region darker than its surroundings (bottom hat region) is obtained by subjecting the grey back side illuminated image to a bottom-hat process. These top hat region and bottom hat region correspond to the region where the print is assumed to be present (assumed print area). Therefore, the control device 60 calculates a sum region of the top hat region and the bottom hat region as the assumed print area where the print is assumed to be present.

After the assumed print area is obtained in Step 2-3, the control flow proceeds to Step 2-4, and the subtraction process is executed. More specifically, a medicament candidate area A where the medicament is assumed to be present (area enclosed by the white line in FIG. 6C) is obtained by calculating the difference between the assumed print and medicament area obtained in Step 2-2 and the assumed print area obtained in Step 2-3. After the medicament candidate area A is obtained in Step 2-4, the noise elimination process is executed at Step 2-5, and noise is eliminated. Next, an image processing to reduce the medicament candidate area A (medicament candidate area reduction process) is implemented at Step 2-6. More specifically, this step calculates a reduced medicament candidate area A2 (region enclosed by the white line in FIG. 6D), which is enclosed by a contour obtained by offsetting the contour that defines the medicament candidate area A toward the inside of the medicament candidate area A. This image processing is implemented as a preprocessing of the image processing that is executed in the inspection area defining step, which will be described in detail later. With this step, the subroutine process shown in FIG. 8 is complete, and the control flow proceeds to Step 1-2 of the main routine shown in FIG. 7.

Figure 9:
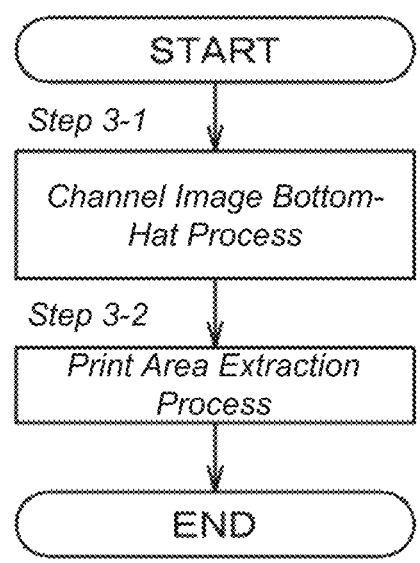
FIG. 9 is a flowchart showing the print candidate area extraction step, which is a subroutine of the medicament information detection process.

Once the control flow of the main routine proceeds to the print candidate area extraction step (Step 1-2), the process (image processing) is implemented in accordance with the subroutine process shown in FIG. 9. More specifically, the subroutine process shown in FIG. 9 includes a channel image bottom-hat process (Step 3-1) and a print area extraction process (Step 3-2) that extract the print candidate area B (region enclosed by the white line in FIG. 6E) from the front side illuminated image.

First in Step 3-1, a bottom-hat process is implemented for each of the R-channel image, G-channel image, and B-channel image that are obtained by the RGB decomposition of the front side illuminated image. A black colored print provided on the pouch b is black colored in all of the R-channel image, G-channel image, and B-channel image. On the other hand, an area corresponding to a dark color medicament that is close to a black color (deep color) is expressed as a color other than black in at least one of the channel images of the R-channel image, G-channel image, and B-channel image. Therefore, the bottom-hat process (channel image bottom-hat process) is first executed for each of the R-channel image, G-channel image and B-channel image in Step 3-1. Next, in Step 3-2, the print candidate area B is obtained from the front side illuminated image by extracting an area that is black in all of the bottom-hatted R-channel image, G-channel image, and B-channel image (print area extraction process). Through this step, the subroutine shown in FIG. 9 is complete, and the control flow proceeds to Step 1-3 in the main routine shown in FIG. 7.

Figure 10:
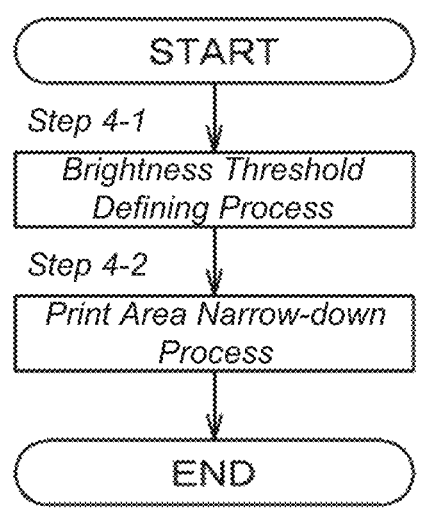
FIG. 10 is a flowchart showing the print area identification step, which is a subroutine of the medicament information detection process.

Once the control flow of the main routine proceeds to the print area identification step (Step 1-3), image processing is implemented in accordance with the subroutine shown in FIG. 10 to specify the print area C. The print area identification step generally includes two processes: brightness threshold defining process (Step 4-1) and print area narrow-down process (Step 4-2).

In the brightness threshold defining process of Step 4-1, the assumed print area (see Step 2-3) obtained in the above-described medicament candidate area extraction step in Step 1-1 is used. In the brightness threshold defining process, the brightness distribution in the assumed print area in the front side illuminated image is analyzed. The assumed print area is an area that corresponds to a text printed on the pouch b. Therefore, by calculating the brightness in this area, it is possible to define the brightness threshold to distinguish the area corresponding to the text from other area, particularly a stamp placed on the medicament or the like. In the present embodiment, the assumed print area obtained in the medicament candidate area extraction step in Step 1-1 is used, and Step 4-1 does not carry out the process of obtaining the assumed print area redundantly. However, the assumed print area may be calculated again in Step 4-1.

After the brightness threshold defining process is complete, the flow moves to the print area narrow-down process of Step 4-2. In this print area narrow-down process, the print candidate area B, which is obtained by the print candidate area extraction step implemented in the above-described Step 1-2, is used. Step 4-2 narrows down the print candidate area B to the text printed on the pouch b as the print area C (see FIG. 6F) by processing the image of the print candidate area B in the front side illuminated image based on the brightness threshold calculated in Step 4-1. Thereby, the print candidate area B is narrowed down to the area corresponding to the text provided on the pouch b as the print area C (see FIG. 6G), and the stamp on the medicament or the like is eliminated. Once the print area narrow-down process of Step 4-2 is complete, the subroutine process shown in FIG. 10 is complete. Then, the control flow proceeds to Step 1-4 of the main routine shown in FIG. 7.

Once the control flow advances to Step 1-4 described above, the control device 60 implements the process that subtracts the print area C obtained in Step 1-3 from the medicament candidate area A obtained in Step 1-1. Thereby, the medicament area X (see FIG. 6H) where the medicament is present is obtained.

Once the medicament area X is obtained in Step 1-4, the control flow proceeds to the inspection area defining step (Step 1-5). In Step 1-5, the area to be inspected is defined based on the medicament area X derived in Step 1-4. More specifically, in Step 1-5, the medicament inspection area Z is obtained by calculating a sum region of the reduced medicament candidate area A2 obtained by the medicament candidate area reduction process (Step 2-6) and the medicament area X obtained in Step 1-4.

The control device 60 recognizes an image contained in the medicament inspection area Z of the front side illuminated image as the image of the medicament present in the pouch b. The control device 60 inspects the image of the medicament to determine whether or not the medicament is correctly packed in accordance with the prescription by implementing the image matching process to the image of the medicament obtained by the above-described control flow with the master image registered in the image database 62.

As described above, to obtain the print area C, the medicament inspection device 10 of the present embodiment first performs the print candidate area extraction step, which narrows down the print candidate area B that is a region containing the print on the pouch b based on the front side illuminated image. Then, in the print area identification step, the medicament inspection device 10 identifies the area corresponding to the print contained in the print candidate area B based on the brightness distribution of the back side illuminated image. In short, the medicament inspection device 10 of the present embodiment narrows down to the print area C from both the front side illuminated image and the back side illuminated image. Therefore, the print area C is obtained with high accuracy.

The medicament inspection device 10 of the present embodiment obtains the medicament area X by subtracting the print area C, specified in the print area identification step, from the medicament candidate area A, obtained in the medicament candidate area extraction step. In addition, as described above, the medicament inspection device 10 can narrow down to the print area C, which corresponds to the print on the pouch b, with high accuracy, distinguishing the print from a stamp on the medicament or the like. Therefore, the medicament inspection device 10 of the present embodiment can identify the medicament area X with high accuracy, and thus the accuracy of the inspection is improved.

The medicament inspection device 10 of the present embodiment can clearly differentiate the assumed print and medicament area from the background area in the medicament candidate area extraction step. This is because the medicament inspection device 10 conducts the dynamic binarization process to the grey back side illuminated image that is obtained from the back side illuminated image. Furthermore, the medicament inspection device 10 can specify the assumed print area in which existence of the print is assumed by acquiring the sum region of the top hat region and bottom hat region, both of which are obtained from the grey back side illuminated image. Then, the medicament inspection device 10 specifies the medicament candidate area A, where existence of the medicament is assumed, by subtracting the assumed print area from the assumed print and medicament area. Therefore the accuracy of specifying the medicament candidate area A is high.

In the print candidate area extraction step, the medicament inspection device 10 specifies the area, which is recognized as being black in all of the R-channel, G-channel, and B-channel images obtained from the front side illuminated image, as a candidate area corresponding to the print placed on the pouch b (print candidate area B). This way of specifying the print candidate area B enables to specify the area corresponding to the print placed on the pouch b with reduced errors.

Upon extracting the print candidate area B as described above, there is a concern that a stamp or the like on the medicament can be included in the extracted print candidate area B. Therefore, the medicament information detection process includes the step (print area identification step), which excludes the area composed of a text or the like that does not constitute the print provided on the pouch b, such as a stamp, from the print candidate area B. The present embodiment utilizes the phenomenon that the brightness of the stamp or the like placed on the medicament and the brightness of the print placed on the pouch b are different from each other in the front side illuminated image. More specifically, the present embodiment analyzes the brightness of the area in the front side illuminated image where the print exists on the pouch b, and defines the brightness value that becomes a threshold that differentiates the print and the stamp or the like. Then, the present embodiment narrows down the print candidate area B in the front side illuminated image to the print area C. Thus, the medicament inspection device 10 can accurately specify the print area C, differentiating the stamp or the like on the medicament and the print on the pouch b. Therefore, the medicament inspection device 10 can accurately identify the medicament area X. Accordingly, the medicament inspection device 10 can perform the inspection of the medicament with high accuracy.

Figure 13:
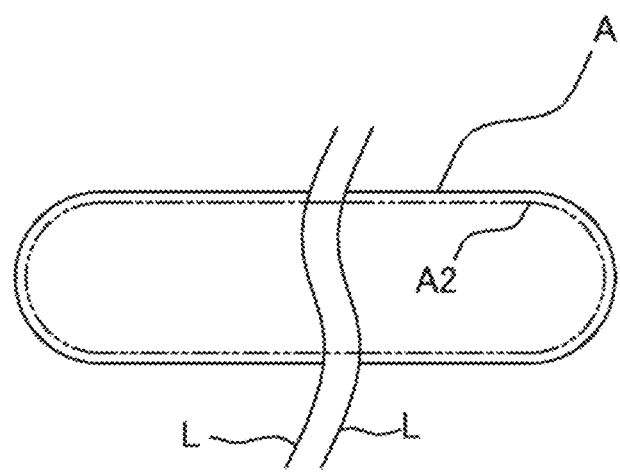
FIG. 13 is an explanatory diagram showing a state of a single medicament, where the image is divided by a striation, which is falsely caused by a wrinkle or a light reflection on the package.

The medicament inspection device 10 of the present embodiment performs the inspection area defining step, which defines the inspection area based on the medicament area X obtained in the medicament area identification step. This inspection area defining step calculates the sum region of the medicament area X and the reduced medicament candidate area A2, which is derived by reducing the medicament candidate area A, to obtain the medicament inspection area Z. By executing such processes, it is possible to resolve the problem shown in FIG. 13 in that there is a possibility that due to the wrinkle on the pouch b, or due to the striation L in the image caused by a light reflection, plural medicament areas X can be recognized although there is only one medicament. Therefore, the inspection accuracy of the medicament can be improved.

<Method of Creating a Master Image of a Divided Medicament>

Figure 11:
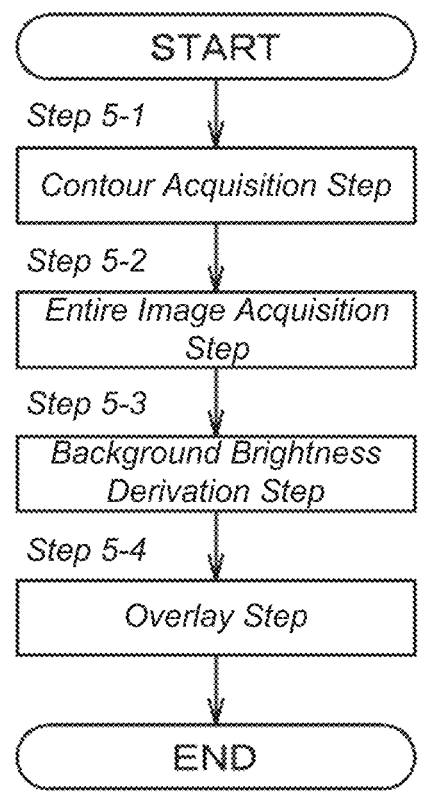
FIG. 11 is a flowchart showing the process of creating a master image of a divided medicament.

Next, the method of creating an image of a divided medicament, which is one of plural divided medicaments, is described. This image of the divided medicament is registered in the image database 62 as a master image and used for inspecting an image of a medicament. The control device 60 is equipped with a master image creation program 64. The master image creation program 64 can create a master image of a divided medicament, which is obtained by dividing the medicament into plurality, based on a master image showing the entire shape of the medicament that is registered in the image database 62. The method of creating a master image of a divided medicament according to the master image creation program 64 is described below on a step-by-step basis referring to the flowchart shown in FIG. 11.

Figure 14A:
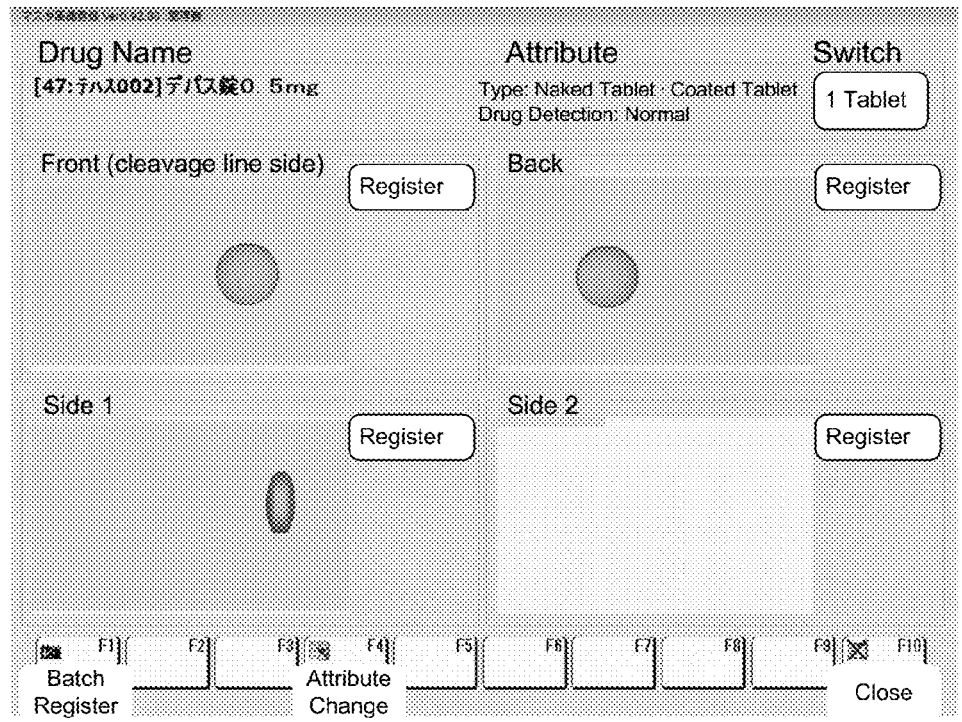
FIGS. 14A and 14B are images showing an interface displayed in the steps of creating the master image of the divided medicament.
Figure 14B:
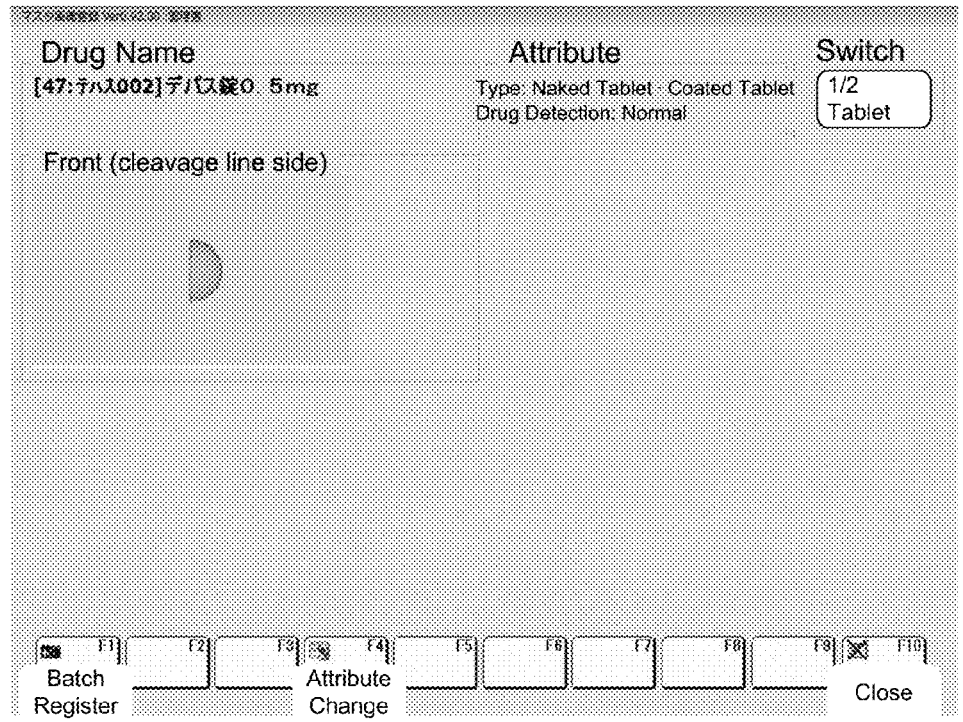

The process of creating the master image of the divided medicament uses the back side illuminated image and the front side illuminated image that capture the entire shape of the medicament, which is also a subject of registration. This process is implemented through a contour acquisition step (Step 5-1), an entire image acquisition step (Step 5-2), a background brightness derivation step (Step 5-3), and an overlay step (Step 5-4). To create the master image of the divided medicament, first, the contour acquisition step is performed in Step 5-1. The contour acquisition step is performed by executing an image processing to obtain a contour of the entire shape of the medicament based on the back side illuminated image that captures the medicament to be registered. This process creates an image which depicts the contour showing the entire shape of the medicament as shown in FIG. 14 A.

Once the contour of the entire shape of the medicament is obtained, the control flow proceeds to Step 5-2, and the entire image acquisition step is implemented. In this step, the medicament inspection device 10 obtains an image of the region inside the contour, which is obtained by the contour acquisition step, from the front side illuminated image showing the appearance of the overall medicament to be registered as an image of the entire shape of the medicament. More specifically, the image of the entire shape of the medicament is obtained by cutting out a portion of the front side illuminated image that corresponds to the area enclosed by the contour obtained in Step 5-1.

Once the image of the entire shape of the medicament is obtained, the control flow proceeds to Step 5-3, and the background brightness derivation step is implemented. In Step 5-3, a portion of the front side illuminated image that corresponds to a region outside of the contour, which is derived in Step 5-1, is recognized as the background image, and the average brightness of the background image is calculated.

Once the average brightness of the background image is obtained, the overlay step is next implemented in Step 5-4. The overlay step is implemented by creating a masking image having the background brightness obtained in Step 5-3, and then overlaying the masking image in an area, which is a portion of the image of the entire shape of the medicament obtained in the entire image acquisition step of Step 5-2. Thereby, a master image of the divided medicament is formed. In the present embodiment, a masking image is overlaid on approximately a half of the image of the entire shape, and the master image of the medicament divided into two that approximately corresponds to a half portion of a tablet is formed. Thereby, as shown in FIG. 14 B, an image showing the shape of the medicament divided into two approximately equally is formed.

<Master Image Substitution Process>

Next, master image substitution process is explained. This process substitutes a master image that has already been registered with a new master image created from an image captured by the camera device. The master image substitution process is a process that is implemented to improve the accuracy of the medicament inspection because, due to individual differences between the camera devices 40 and the illuminating devices 50, there is a possibility that color tone or the like can be different even if the same medicament is photographed. In other words, the master image substitution process is a process to minimize the error of specifying the medicament due to differences of color tone or the like between the master image registered in the image database 62 and the image actually captured by the camera device 40.

Figure 12:
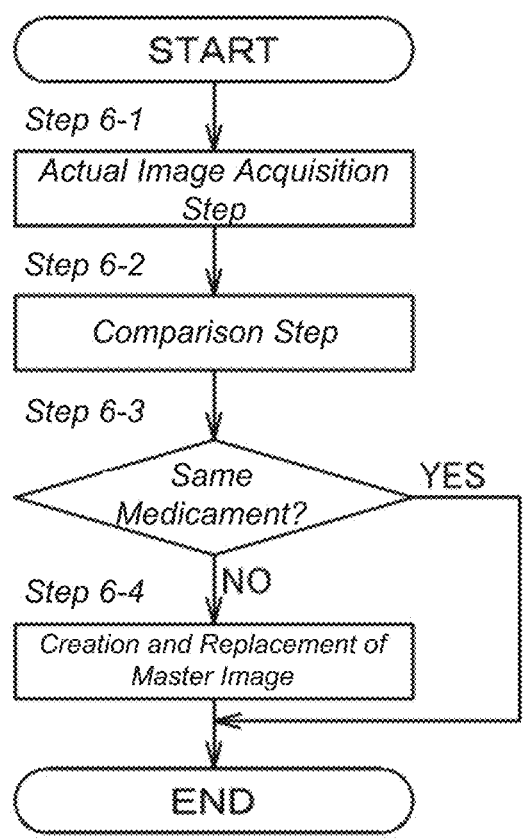
FIG. 12 is a flowchart showing the process of replacing the master image of the medicament.

As shown in the flowchart of FIG. 12, to execute the master image substitution process, first, an actual image acquisition step (Step 6-1) is implemented to obtain an actual image of the medicament by placing the medicament, which is the substitute candidate of master image, in the inspection section 32, and then capturing the image of the medicament with the camera device 40. Next, at Step 6-2, a comparison step is implemented to compare the actual image of the medicament obtained in the actual image acquisition step with the master image of the corresponding medicament registered in the image database 62. If it is determined that both the medicaments are different medicaments (in the case of "No" in Step 6-3), a master image is created based on the actual image of the medicament obtained by photographing with the camera device 40, and the master image already registered is substituted with this newly created master image (Step 6-4). On the other hand, when both the medicaments are determined as the same medicament, as the comparison result of Step 6-2 (in the case of "Yes" in Step 6-3), the control flow is terminated without replacing the registered master image with the actual image of the medicament.

The master image substitution process described above enables to prevent inspection error due to the color tone differences or the like between the master image registered in the image database 62 and the captured image obtained by actually photographing the medicament.

The present invention is not limited to the above-described embodiments or the examples described above. A person skilled in the art could easily understand that other embodiments could be obtained from the suggestions and spirit of the present invention without departing the scope of the claims.

The invention claimed is:

1. A medicament inspection device comprising:
    an inspection section where a medicament enclosed in a package is placed;
    an illuminating device for illuminating the package placed in the inspection section;
    a camera device for taking images of the package placed in the inspection section and illuminated by the illuminating device; and
    a control device for executing a medicament information detection process to detect a number and/or a type of the medicament enclosed in the package, as medicament information, by performing an image matching process using the images taken by the camera device;
    wherein the illuminating device comprises:
        a front side illuminating device for illuminating the package from a side where the camera device is located, and
        a back side illuminating device for illuminating the package from a side opposite to the camera device;
    wherein the images taken by the camera device include:
        a front side illuminated image, which is an image of the package taken by the camera device with the front side illuminating device being ON, and
        a back side illuminated image, which is an image of the package taken by the camera device with the back side illuminating device being ON; and
    wherein the control device executes the medicament information detection process by performing the following steps:
        a medicament candidate area extraction step comprising extracting a dark colored area in the back side illuminated image as a medicament candidate area A where the medicament is assumed to be present,
        a print candidate area extraction step comprising extracting an area containing a print on the package based on the front side illuminated image as a print candidate area B,
        a print area identification step comprising identifying an area corresponding to the print contained in the print candidate area B as a print area C based on a brightness distribution of the back side illuminated image, and
        a medicament area identification step comprising identifying a medicament area X by subtracting the print area C from the medicament candidate area A.

2. The medicament inspection device of claim 1, wherein in the medicament candidate area extraction step, the control device performs the steps of:
    obtaining a grey back side illuminated image by converting the back side illuminated image into a grey scale image,
    specifying an assumed print and medicament area where the print and the medicament are assumed to be present by binarizing the grey back side illuminated image,
    calculating a sum region of a top hat region obtained by top-hat processing the grey back side illuminated image and a bottom hat region obtained by bottom-hat processing the grey back side illuminated image, as an assumed print area where the print is assumed to be present, and
    obtaining the medicament candidate area A from a difference between the assumed print and medicament area and the assumed print area.

3. The medicament inspection device of claim 1, wherein in the print candidate area extraction step, the control device performs the steps of:
    bottom-hat processing all the images of an R-channel image, a G-channel image, and a B-channel image that are obtained by an RGB decomposition of the front side illuminated image, and
    extracting an area that is assumed to be black in all the images of the R-channel image, the G-channel image, and the B-channel image as the print candidate area B.

4. The medicament inspection device of claim 1, wherein in the print area identification step, the control device performs the steps of:
    obtaining a brightness distribution in an assumed print area, where the print is assumed to be present, in the front side illuminated image,
    defining a brightness threshold for distinguishing an area corresponding to the print and other area, and
    narrowing down the print candidate area B in the front side illuminated image to the print area C based on the brightness threshold defined.

5. The medicament inspection device of claim 1, wherein the control device further performs an inspection area defining step comprising defining a medicament inspection area Z, which is an area to be inspected, based on the medicament area X, and wherein in the inspection area defining step, the control device performs the steps of:
    obtaining a reduced medicament candidate area A2, which is a reduced area of the medicament candidate area A, and
    calculating a sum region of the medicament area X and the reduced medicament candidate area A2 as the medicament inspection area Z.

6. The medicament inspection device of claim 1, wherein the control device performs an image matching using an image database, in which master images of medicaments are stored, for detecting the medicament information,
  wherein the control device further performs a master image creation process for creating a master image of a divided medicament from a master image including an entire shape of the medicament and storing the master image of the divided medicament in the image database, and
  wherein in the master image creation process, the control device performs the steps of:
  a contour acquisition step of acquiring a contour of the entire shape of the medicament based on the back side illuminated image of the medicament,
  an entire image acquisition step of acquiring an image in an area inside the contour in the front side illuminated image as an image of the entire shape of the medicament,
  a background brightness derivation step of recognizing an image in an area outside the contour in the front side illuminated image as a background image, and calculating an average brightness of the background image, and
  an overlay step of creating a masking image having a brightness corresponding to the average brightness of the background image, and overlaying the masking image on a portion of the image of the entire shape of the medicament to obtain the master image of the divided medicament.

7. The medicament inspection device of claim 1, wherein the control device performs a comparison process using an image database, in which a master image of the medicament is stored, and
  wherein in the comparison process, the control device performs the steps of:
  comparing an image of a medicament placed in the inspection section and taken by the camera device with the master image of this medicament stored in the image database;
  determining if the medicament in the master image and the medicament in the image taken by the camera device are different from each other,
  creating a new master image of the medicament from the image taken by the camera device when the control device determines that both the medicaments are different from each other, and
  replacing the master image of the medicament stored in the image database with the master image of this medicament newly created.

8. A medicament packing system, comprising:
  a medicament packing device for packing medicaments in a package in accordance with a prescription; and
  the medicament inspection device of claim 1,
  wherein the medicament inspection device counts a number of the medicaments packed in the package by the medicament packing device.

9. A device for updating a master image of a medicament stored in a database;
  comprising:
  a camera device for taking an image of a medicament; and
  a control device capable of accessing the database,
  wherein the control device performs the steps of:
  comparing the image of the medicament taken by the camera device with the master image of this medicament stored in the database,
  determining if the medicament in the master image and the medicament in the image taken by the camera device are different from each other,
  creating a new master image of the medicament from the image taken by the camera device when the control device determines that both the medicaments are different from each other, and
  replacing the master image of the medicament stored in the database with the master image of this medicament newly created.

* * * * *